United States Patent

Filipovic et al.

Patent Number: 5,515,845
Date of Patent: May 14, 1996

[54] CANISTER FOR THE RECOVERY OF HALOGENATED HYDROCARBONS IN A GAS STREAM

[75] Inventors: Dusanka Filipovic, Willowdale; Fraser Sweatman, Toronto, both of Canada

[73] Assignee: Praxair Canada Inc., Mississuaga, Canada

[21] Appl. No.: 50,687

[22] Filed: Apr. 22, 1993

Related U.S. Application Data

[62] Division of Ser. No. 640,525, Jan. 11, 1991, Pat. No. 5,231,980, which is a continuation of Ser. No. 162,450, Mar. 1, 1988, abandoned.

[30] Foreign Application Priority Data

Mar. 4, 1987 [CA] Canada ..................................... 531133

[51] Int. Cl.$^6$ ..................................................... A62B 7/10
[52] U.S. Cl. ................................ 128/205.12; 128/203.12
[58] Field of Search ......................... 128/203.12, 204.16, 128/205.12, 205.28

[56] References Cited

U.S. PATENT DOCUMENTS

| | | | |
|---|---|---|---|
| 3,469,011 | 9/1969 | Terrell | 514/722 |
| 3,527,813 | 9/1970 | Terrell | 568/684 |
| 3,535,388 | 10/1970 | Terrell | 568/684 |
| 3,535,425 | 10/1970 | Terrell | 514/722 |
| 3,592,191 | 7/1971 | Jackson | 128/203.28 |
| 3,729,902 | 5/1973 | Ventriglio et al. | 96/127 |
| 3,867,936 | 2/1975 | Kelley | 128/205.12 |
| 3,941,573 | 3/1976 | Chapel | 96/135 |
| 4,350,662 | 9/1982 | Dowgul et al. | 128/205.12 |
| 5,231,980 | 8/1993 | Filipovic et al. | 128/205.12 |

FOREIGN PATENT DOCUMENTS

| | | |
|---|---|---|
| 1195258 | 10/1985 | Canada . |
| 185876 | 2/1978 | Czechoslovakia . |

*Primary Examiner*—Edgar S. Burr
*Assistant Examiner*—Aaron J. Lewis
*Attorney, Agent, or Firm*—Stanley Ktorides

[57] ABSTRACT

A process for the recovery of halogenated hydrocarbons from a gas stream comprises passing the gas stream through a bed of hydrophobic molecular sieve adsorbent, preferably of the high silica zeolite type. Such adsorbent has pore diameters large enough to permit molecules of the halogenated hydrocarbons to pass therethrough and be selectively adsorbed in the large internal cavities of the crystal framework, whereby the halogenated hydrocarbons are removed. The gas is continued to be passed through the bed of adsorbent material until the material is saturated to the extent that breakthrough of the hydrocarbons is determined. The adsorbent material with adsorb phase of halogenated hydrocarbons is removed from the machine and regenerated by exposing the saturated material to an inert purging gas stream under conditions which desorb the halogenated hydrocarbons from the adsorbent material into the purging gas stream. The halogenated hydrocarbons are then removed from the purging gas stream and purified to a purity for reuse of the recovered halogenated hydrocarbons.

5 Claims, 6 Drawing Sheets

CANISTER FOR THE RECOVERY OF HALOGENATED HYDROCARBONS IN A GAS STREAM

This is a Continuation-in-Part of prior U.S. application Ser. No. 640,525 Filing Date: Jan. 11, 1991, now U.S. Pat. No. 5,231,980 which in turn is a continuation of application Ser. No. 162,450 Filing Date Mar. 1, 1988 now abandoned.

FIELD OF THE INVENTION

This invention relates to the recovery of halogenated hydrocarbons from a gas stream and recovery thereof for reuse.

BACKGROUND OF THE INVENTION

Halogenated hydrocarbon compounds include the family of compounds of bromo-, fluoro- and/or chloroethers, fluorinated alkyl ethers, chlorofluorocarbons and chlorofluoro ethers and their derivatives. This family of compounds are typically used as solvents, refrigerants, anesthetic gases, aerosol propellants, blowing agents and the like. Many of these compounds are widely used and normally discharged into the atmosphere. However, if these compounds could be recovered and re-used there would be a considerable cost saving and reduction in environmental pollution. In view of the possible effects of released anesthetic gases, attempts have already been made to recover such gases.

An example of anesthetic gas removal, is with regard to patient exhalent to ensure that the environment in the operating theatre does not contain anesthetic gases which can have a long term effect on the professionals conducting the operation. Commonly, anesthetic gases are removed from patient exhalent by use of various types of disposable absorbers, such as that disclosed in U.S. Pat. Nos. 3,867,936 and 3,941,573. In the United States patent to Kelley, U.S. Pat. No. 3,867,936, an absorber unit is in the shape of a hollow drum filled with activated carbon to absorb anesthetic gases exhaled by the patient. When the weight of the absorber unit increases to a predetermined value, the unit is replaced with a fresh one. In Chapel, U.S. Pat. No. 3,941,573, a molecular sieve is used in combination with the activated carbon in a disposable cartridge. The cartridge is included in the patient anesthetic administration breathing system to absorb on both the activated carbon and the molecular sieve materials the exhaled anesthetic gases.

It is common to dispose of the absorber units used to absorb anesthetic gases. However, in view of the rising costs of the anesthetic gases, attempts are being made to recover them. For example, in U.S. Pat. No. 3,592,191, a system is provided for recovering exhausted anesthetic gases from patient exhalent by removing water vapor from the collected gases by their condensation thereof or with a hygroscopic material. This treated gas then has the anesthetic agent extracted therefrom by a cryogenic process in which the vapors of the anesthetic gases are condensed to liquid phase, or by removal on an absorbent material which is processed later to remove the anesthetic agents. The collected anesthetic liquids are then reintroduced directly into the anesthetic system. Such approach has little if any facility to control bacterial contamination and recycle of harmful microorganisms to the patient.

Another approach in the recapture of anesthetic gases is disclosed in Czechoslovakian patent 185,876. An absorbent material is used to absorb halogenous inhalant anesthetics from the patient exhalent. When the adsorbent material is saturated, it is removed in an appropriate container and placed in a regeneration system. A purging gas, such as steam, is used to remove the anesthetic agents from the adsorbent material. The purged gas is then collected with water removed therefrom and the separated anesthetic agents are subjected to fractionation to separate out the individual anesthetic agents from the supply of anesthetic gases from various operating theatres.

The use of molecular sieves to adsorb gaseous components is exemplified in U.S. Pat. No. 3,729,902. Carbon dioxide is adsorbed on a molecular sieve which is regenerated with heated steam to remove the carbon dioxide from the adsorbent material. Another example of the use of molecular sieves to adsorb organic materials is disclosed in Canadian patent 1,195,258. In this instance, a hydrophobic molecular sieve is used to adsorb organic species from a gas stream containing moisture. The hydrophobic molecular sieve selectively adsorbs the organic molecular species into the adsorbent material, while preventing the collection of water vapor from the gas stream on the adsorbing material. The temperature and pressure at which the system is operated is such to prevent capillary condensation of the water in the gas stream onto the adsorbing material. By removing the adsorbing material from the system, the adsorbing material is essentially free of water yet has absorbed thereon the desired organic molecular species. The organic molecular species are then recovered from the adsorbent material by purging.

Particularly desirable types of anesthetic gases are commonly sold under the trade marks ETHRANE and FORANE, as disclosed in U.S. Pat. Nos. 3,469,011; 3,527,813; 3,535,388; and 3,535,425. These types of anesthetic gases are particularly expensive; hence an effective method of recovering them from patient exhalent for reuse would be economically advantageous.

SUMMARY OF THE INVENTION

According to an aspect of the invention, a process for the recovery of halogenated hydrocarbons from a gas stream is provided. The process comprises passing the gas stream through a bed of hydrophobic molecular sieve adsorbents having pore diameters large enough to permit molecules of the halogenated hydrocarbon to pass therethrough and be adsorbed in the large internal cavities of the crystal framework, whereby the halogenated hydrocarbons are removed from the gas stream. The gas stream is passed through the bed of adsorbent material at least until just prior to breakthrough of an essentially saturated halogenated hydrocarbon absorption front. The adsorbent material containing the adsorbed phase is regenerated by exposing it to an inert purging gas stream whereby the halogenated hydrocarbons are desorbed into the purging gas stream. The halogenated hydrocarbons are removed from the purging gas stream and are purified to a purity suitable for reuse.

According to another aspect of the invention, a canister is provided for use in adsorbing halogenated hydrocarbons from a gas stream passed through the canister. The canister has a peripheral side wall, a first end wall with an inlet port and a second end wall with an outlet port. A first fine mesh screen is spaced from the first end wall and closes off the first canister end. A second fine mesh screen is spaced from the second end wall and closes off the second canister end. Hydrophobic molecular sieve granular adsorbents are packed in the canister between the first and second screens. The sieve adsorbents have pore diameters large enough to permit molecules of the halogenated hydrocarbons to pass therethrough and be adsorbed in the large internal cavities of the crystal framework, whereby the halogenated hydrocarbons are removed from the gas stream. The first and second screens have a mesh sizing to retain the granular material in the canister. A means is provided for resiliently urging one of the first or second screens towards the other to compress such granular material between the screens.

According to another aspect of the invention, an anesthetic machine is provided having an inlet port of the canister connected to an exhaust port of the machine thereby passing patient exhalent from the anesthetic machine to the canister to absorb anesthetic gases.

According to another aspect of the invention, an apparatus is provided for regenerating the canister of adsorbent as connected to an anesthetic machine comprising means for connecting an incoming line of nitrogen gas to the inlet. A means is provided to heat the canister and optionally the nitrogen gas in the incoming line to a temperature in the range of 30° C. to 150° C. Means is provided for connecting an outgoing line to the canister outlet and for measuring temperature of nitrogen gas enriched with the desorbed anesthetic in the outgoing line. Regeneration is ceased shortly after the temperature of the nitrogen gas in the outgoing line is at a level of the temperature of the nitrogen gas in the incoming line.

BRIEF DESCRIPTION OF THE DRAWINGS

Preferred embodiments of the invention are shown in the drawings wherein.

DETAILED DESCRIPTION OF THE PREFERRED EMBODIMENTS

Figure 1:
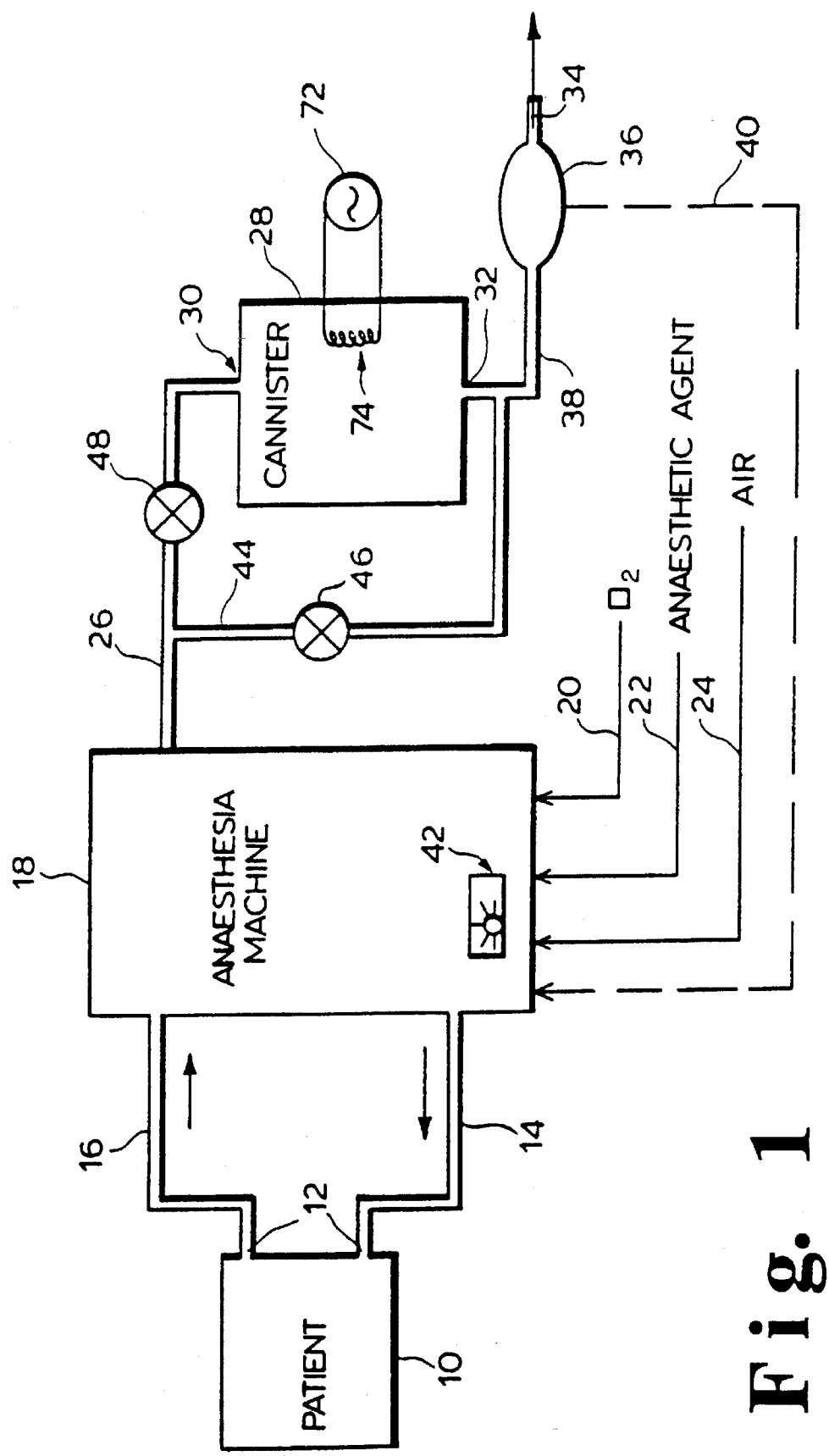
FIG. 1 is a schematic of an anesthetic machine with canister connected thereto for removing anesthetics from the patient exhalent.

According to the invention, a system is provided which can recover a variety of halogenated hydrocarbons and purify the recovered compounds. Typical halogenated hydrocarbons include bromo-, chloro- and/or fluoroethers, fluorinated alkyl ethers, chlorofluorohydrocarbons, chlorofluoroethers and their derivatives. Anesthetic gases are well known types of halogenated hydrocarbons which include isoflurane, enflurane, halthane, and methoxyflurane. Other well known halogenated hydrocarbons include the variety of Freons (trade mark) such as trichlorofluromethane, and dichlorodifluoromethane. This family of halogenated hydrocarbon compounds which include, for example, an alkyl group or ether group substituted with one or more of chloro, fluoro and bromo groups are readily absorbed on the high silica zeolite adsorbent and can be readily desorbed from the adsorbent. A preferred aspect of the invention is described with respect to the recovery of various anesthetic gases. It is appreciated that the principles of the invention which are demonstrated by the following embodiments are equally applicable to the recovery of other types of halogenated hydrocarbons.

A variety of organic based anesthetics are used in patient surgery. Common forms of anesthetics are those sold under the trade marks ETHRANE and FORANE by (ANAQUEST of Quebec, Canada). The respective chemical formulae for these anesthetics are as follows: 1,1,2-trifluoro-2-chloroethyl difluoromethyl ether and 1-chloro-2,2,2-trifluoroethyl difluoromethyl ether. Other types of anesthetics are, for example, Halothane (trade mark) of the formula bromochlorotrifluoroethane and Penthrane (trade mark) of the formula 2,2-dichloro- 1,1-difluoroethyl methyl ether which are readily available from various suppliers, such as, Hoechst, Ayerst, Abbott, etc.

By way of an anesthetic machine, these anesthetics either singularly or in combination are delivered to the patient in combination with oxygen, nitrous oxide and/or air. As the patient breathes the gas stream containing the anesthetic, a desired degree of unconsciousness is achieved and monitored by an anesthetist. Not all of the anesthetic inhaled by the patient is absorbed into the blood system. In fact, very little of the anesthetic is absorbed. During procedures, the gas flow rate to the patient may be in the range of 0.5 to 7 liters per minute, where the concentration by volume of the anesthetic may be in the range of 0.3% to 2.5%. Normally, the patient exhalent is not recycled via the anesthetic machine. Instead, it is exhausted to the atmosphere by way of appropriate ducting. It is very important to ensure that the patient exhalent is not exhausted into the operating theatre, because the presence of the anesthetics can have a long term effect on the people in the operating room. It is appreciated that the use of the term patient is in a general sense. It is understood that anesthesia is practiced on a variety of mammals not only including humans but also animals such as horses, cattle and other forms of livestock, domestic pets and the like.

As shown in FIG. 1, the patient represented at 10 is connected to a mask 12 having a gas line 14 communicating therewith. The desired mixture of anesthetic gas is delivered in line 14 to the patient 10. The patient exhalent is delivered in line 16 to the anesthetic machine 18. The anesthetic machine 18, which is supplied with oxygen, a source of anesthetic and air in lines 20, 22 and 24, is operated to introduce the desired mixture in line 14. The patient exhalent in line 16 is discharged via line 26. Normally line 26 leads to external ducting for exhausting the anesthetics to atmosphere. In accordance with this invention, a canister 28 having an inlet 30 and an outlet 32 is interposed in line 26 at a position sufficiently downstream of the machine so as to have no or minimal effect on its operation. The patient exhalent in line 26, therefore, flows through the canister 28 before exhausting to atmosphere at 34. The canister 28 is charged with a hydrophobic molecular sieve granular material of silicalite which adsorbs from the patient exhalent stream the organic gaseous anesthetic. Hence, the stream discharge at 34 is free of the anesthetic gases.

An anesthetic sensor 36 may be provided in the exhaust line 38 to sense the presence of anesthetics exiting from the canister 28. It is appreciated that the adsorption front of the adsorbed anesthetics, in the bed of adsorbent travels along the bed towards the canister outlet. Such adsorption front will usually have a curved profile across the canister as it approaches the outlet. The curved profile normally assumes an elongated "S" shape. The sensor will sense when any portion of that front has broken through the adsorbent into the outlet. Replacement of the canister is normally required at this time though the bed of adsorbent is not entirely saturated with organic anesthetic. The sensor 36 may be connected via signal line 40 to the anesthetic machine 18. The anesthetic machine may be equipped with a light and/or audible alarm 42 which is actuated when the sensor 36 senses anesthetic gases in line 38. This indicates to the anesthetist that the canister 28 should be replaced so that continued recovery of anesthetics is achieved. It is appreciated that a bypass 44 controlled by valve 46 may be provided to route the patient exhalent past the canister 28 during replacement thereof. In this instance, a valve 48 is provided in line 26 to shut off the supply to canister 28 during replacement of the canister.

The canister may be charged with any of a variety of adsorbents. However, according to an aspect of this invention, the molecular sieve adsorbent utilized has an adsorptive preference for the less polar organic materials with respect to water, i.e., be hydrophobic. In the case of zeolitic molecular sieves, as a general rule the more siliceous the zeolite, the stronger the preference for non-polar adsorbate species. Such preference is usually observable when the framework molar $SiO_2/Al_2O_3$ ratio is at least 12, and is clearly evident in those zeolite species having $SiO_2/Al_2O_3$ ratios of greater than 50. A wide variety of zeolites can now be directly synthesized to have $SiO_2/Al_2O_3$ ratios greater than 50, and still others which cannot at present be directly synthesized at these high ratios can be subjected to dealumination techniques which result in organophilic zeolite products. High temperature steaming procedures involving zeolite Y which result in hydrophobic product forms are reported by P. K. Maher et al., "Molecular Sieve Zeolites", Advan. Chem. Ser., 101, American Chemical Society, Washington, D.C., 1971, p. 266. A more recently reported procedure applicable to zeolitic species generally involves dealumination and the substitution of silicon into the dealuminated lattice site. This process is disclosed in U.S. Pat. No. 4,503,023 issued Mar. 5, 1985 to Skeels et al. Many of the synthetic zeolites prepared using organic templating agents are readily prepared in a highly siliceous form—some even from reaction mixtures which have no intentionally added aluminum. These zeolites are markedly organophilic and include ZSM-5 (U.S. Pat. No. 3,702,886); ZSM-11 (U.S. Pat. No. 3,709,979); ZSM-12 (U.S. Pat. No. 3,832,449) and ZSM-35 (U.S. Pat. No. 4,016,245) to name only a few. It has been found that the silica polymorphs known as silicalite, F-silicalite and TEA-silicalite are particularly suitable for use in the present invention and are thus preferred, though not, strictly speaking, zeolites, because of a lack of ion-exchange capacity, these molecular sieve materials are included within the terms zeolite or zeolitic molecular sieve as used herein. These materials are disclosed in U.S. Pat. No. 4,061,724; U.S. Pat. No. 4,073,865 and U.S. Pat. No. 4,104,294, respectively.

Figure 2:
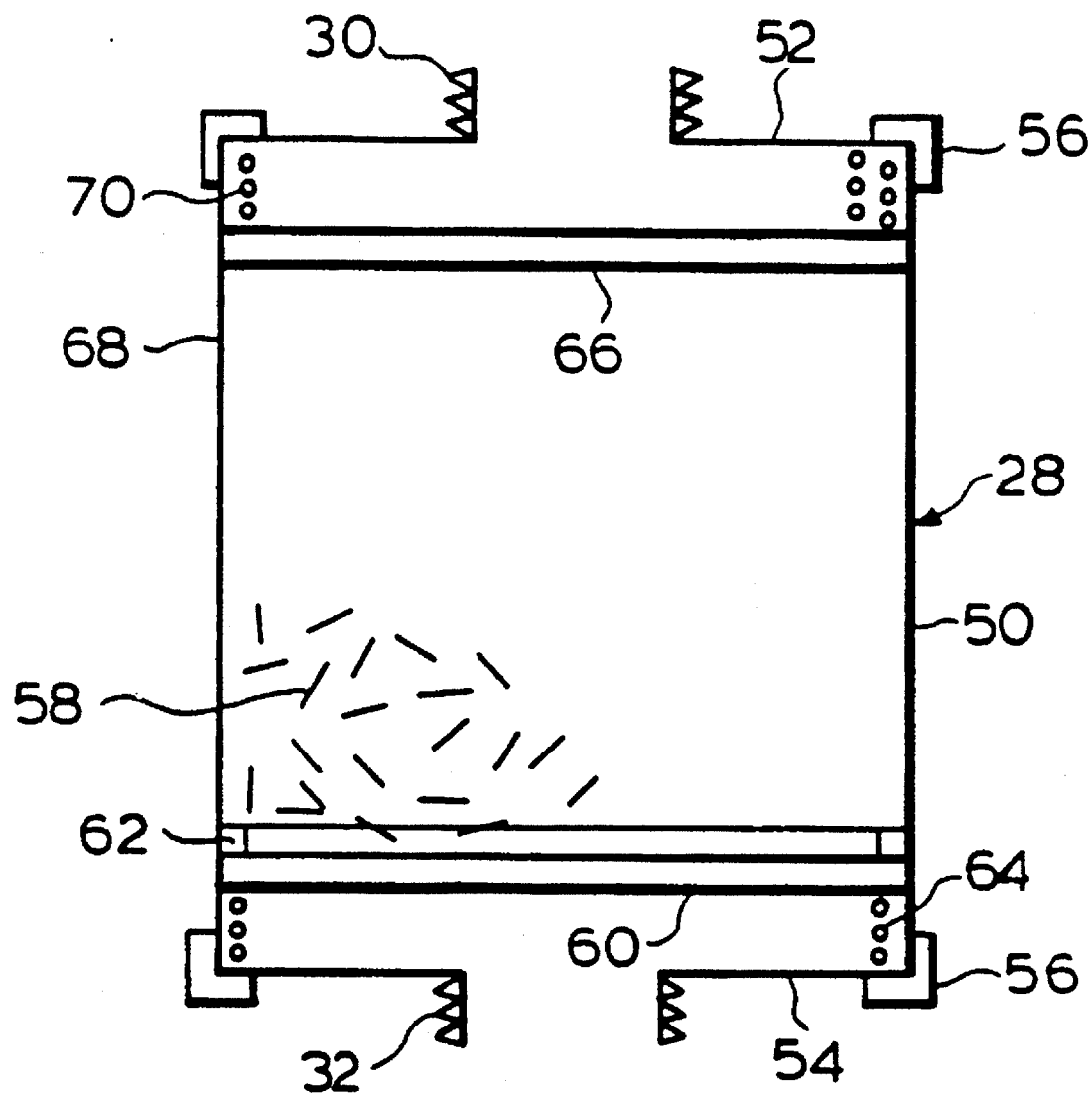
FIG. 2 is a section through the canister of FIG. 1.

As shown in FIG. 2, the canister 28, which may be cylindrical in shape, has a side wall 50 with a first end 52 having an inlet 30. A second end 54 has the outlet 32. It is appreciated that the canister 28 may be disassembled by having releasable fasteners 56 about the perimeter of the side wall 28 to clip respectively the first and second end walls 52 and 54 to the side wall 50. Within the canister 28, the hydrophobic molecular sieve granular material of silicalite 58 is contained. At the second end of the canister, a fine mesh screen 60 is positioned to close off the second end defined by flange 62. The fine mesh screen 60 conforms to the interior shape of the canister side wall 50 which, in this instance, is circular and abuts the flange 62. A coiled spring 64, as spaced between the wall 54 and the fine mesh screen 60, holds the screen in place against the flange 62. With the other end 52 and the fine mesh screen 66 removed, the silicalite material 58 may be charged into the canister 28. Once the silicalite material has achieved a level indicated by arrow 68, the screen 66 is placed in the canister. A spring 70 is positioned between the wall 52 and the screen 66. When the clips 56 are clamped in position, the spring pushes the fine mesh screen 66 against the silicalite material 58 to compress and hold the silicalite material in place in the canister 28. This ensures that the silicalite material remains relatively fixed in the canister during use.

The patient exhalent in line 26 from the anesthetic machine 18 of FIG. 1 is naturally moist. This has presented significant problems in the past in attempting to recover organic anesthetics from the moist patient exhalent. It has been discovered that the use of a hydrophobic molecular sieve granular material of silicalite overcomes those problems. The silicalite material has a pore diameter which permits the material to selectively adsorb and remove the organic gaseous anesthetic from the humid patient exhalent and which minimizes coadsorption of water molecules in the patient exhalent. The benefits in using silicalite adsorbents is that there is no bacterial growth on the adsorbents which can become a problem because of the presence of bacteria in the patient exhalent. The adsorbent is non-flammable in the presence of oxygen. This is a significant drawback with organic forms of adsorbents since for certain concentrations of oxygen, the organic adsorbents are at least flammable if not explosive. The silicalite adsorbent is inert so that minimal if any decomposition of the anesthetic agent is induced whereas with organic adsorbents, such as activated carbon, hydrochloric acid can be produced in the presence of iron by way of decomposition of the halogenated anesthetics. The inert silicalite adsorbents are readily re-sterilized using ozone, steam, peroxide or other disinfectants without in any way affecting the adsorptive reuse characteristics of the adsorbent. The silicalite adsorbents are found to be microwave transparent. Therefore, regeneration can be accomplished using microwave heating.

A preferred form of silicalite is that manufactured and sold by Union Carbide under the trade mark "S-115 Silicalite". The chemical properties of S-115 Silicalite are as follows:

Chemical properties (greater than) 99% $SiO_2$ (less than) 1% aluminum oxide.

The Silicalite has the following physical properties:

| Free aperture | |
|---|---|
| Zig-zag channels | 5.4 A |
| Straight channels | 5.75 × 5.15 A |
| Pore volume | 0.19 cc/gm |
| Pore size | approx. 6 angstroms in diameter |
| Crystal density | 1.76 gm/cc |
| Largest molecule adsorbed | Benzene |
| Form | Powder, Bonded Bead or Pellet |

By use of a silicalite material having those properties, it has been discovered that the organic anesthetics are adsorbed by the silicalite while other components of the patient exhalent, including moisture, pass through. Hence, a minimum of moisture is retained in the canister. Supplemental heating of the canister 28, as shown in FIG. 1, may be provided by control 72 for heater 74. The purpose of the heat is to ensure that the canister 28, during use on the anesthetic machine, remains at a temperature which prevents the moisture in the patient exhalent condensing on the silicalite material in the canister and also on the canister surfaces.

Figure 3:
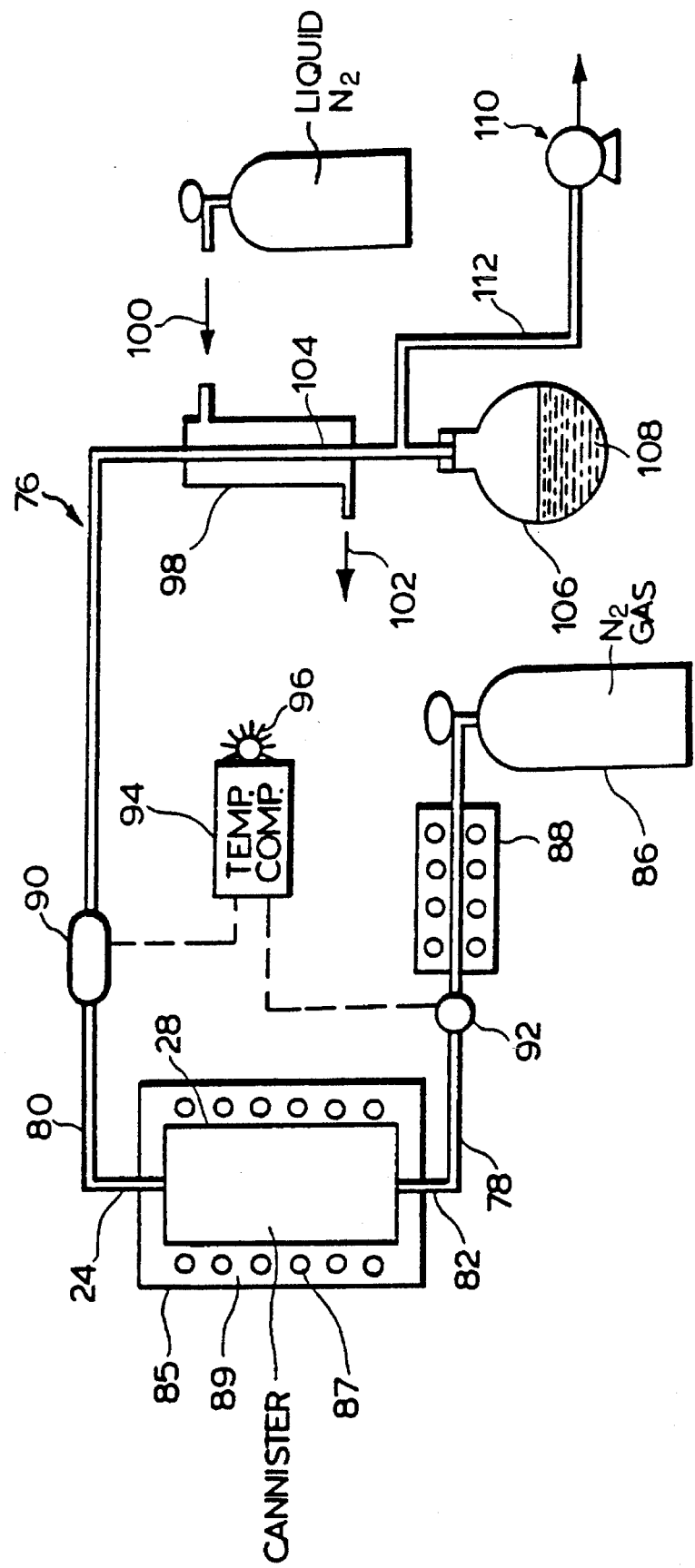
FIG. 3 is a schematic of the apparatus used to regenerate the adsorbent material in the canister of FIG. 2.

Once it has been determined that the silicalite material in the canister is saturated with adsorbed organic anesthetic, or that the adsorption front has broken through to the outlet, the canister has to be replaced in the manner discussed. To regenerate the silicalite material in the canister 28 and to recover the anesthetic components for reuse, a silicalite regeneration system 76 is shown in FIG. 3. The system permits interposing canister 28 in lines 78 and 80 by couplings 82 and 84 which connect to the inlet and outlet 30 and 32 of the canister 28. The canister may be optionally heated within a conventional oven 85. An inert purging gas is passed through the silicalite material of the canister 28 to desorb the organic anesthetics from the silicalite granular material. In accordance with a preferred aspect of this invention, nitrogen gas or air is used as the purging gas. To enhance the desorption of the adsorbed organic anesthetics, the silicalite material is preferably heated to a temperature range of 30° C. to 150° C. It is appreciated that with other types of halogenated hydrocarbons, different temperature ranges may be necessary to effect desorption of the compounds.

In order to heat the silicalite material within the canister to this temperature the oven 85 having heating coils 87 surrounded by insulating material 89 is controlled on the basis of prior experimentation in a manner to ensure that the silicalite is in this temperature range for passing of the purging gas through the canister. It is understood that in view of the transparency of the silicalite adsorbent to microwaves, then a microwave oven may be substituted for the conventional oven 85.

The silicalite material in canister 28 during regeneration may either be heated by direct application of heat to the canister or by heating the nitrogen gas or air purging stream. In accordance with the embodiment shown in FIG. 3, the nitrogen gas from the source 86 may also be heated in heater 88 to a desired temperature in the range of 30° to 150° C. The purging gas passes through the silicalite material of the canister 28 where the fine mesh screen, as shown in FIG. 2, serve to retain the silicalite material in the canister. Hence any desired flow rate of purging gas may be used. The purging gas exits the canister 28 through line 80 and passes through a temperature sensor 90. Temperature sensor 90 provides an indication of the temperature of the purging gas in line 80. When the temperature of the purging gas in the exit line achieves a temperature nearing that of the temperature in the entrance lines 78, it has been determined that the silicalite material is at a temperature approximating the inlet temperature and that most of the organic anesthetic is desorbed. The system is then run for a desired period of time beyond that point to complete desorption. That aspect of the process may be automated and a temperature sensor 92 may be included in the inlet side to measure the temperature of the incoming stream. By way of suitable microprocessor, the signals from temperature sensors 90 and 92 may be fed to a control system 94 which compares the temperatures and actuates a signal 96 to indicate that canister regeneration is complete. It is appreciated, that regeneration of the silicalite adsorbent may take place at lower temperatures outside of the preferred range. For example, regeneration of absorbent can be achieved at temperatures as low as 25° C. where the time for regeneration is thereby extended.

It is appreciated that in the alternative, silicalite adsorbent carrying anesthetic compounds may be removed from the canister and placed with adsorbent removed from other canisters. The collected adsorbent may then be regenerated in a separate vessel in a manner as discussed with respect to a single canister.

The purging gas continues in line 80 through condenser 98. The purpose of the condenser is to remove, in liquid form, the organic anesthetics from the purging gas. Liquid nitrogen at a cryogenic temperature is fed through the condenser 98 via its inlet 100 and exit 102. This provides sufficiently cool temperatures in the line 104 of the condenser to cause the organic anesthetics to condense and permits collection in vessel 106 of liquid form anesthetics 108. To assist in the condensing of the organic anesthetics, a partial vacuum is drawn in line 104 by vacuum pump 110 connected to line 104 via line 112. The condensed liquid 108 then consists primarily of the organic anesthetics. In the course of one day, several operations may be conducted involving the same anesthetic machine 18. It may require many operations to saturate the canister 28 with anesthetics from the patient exhalent. During the different operations, it is appreciated that different anesthetics may be used. For example, Forane (trade mark) or Ethrane (trade mark) may be used separately or in combination with or without Halothane (trade mark). When the canister is saturated, two or more gases may be present inside. Hence, liquid 108 will correspondingly consist of a mixture of anesthetic components.

Figure 4:
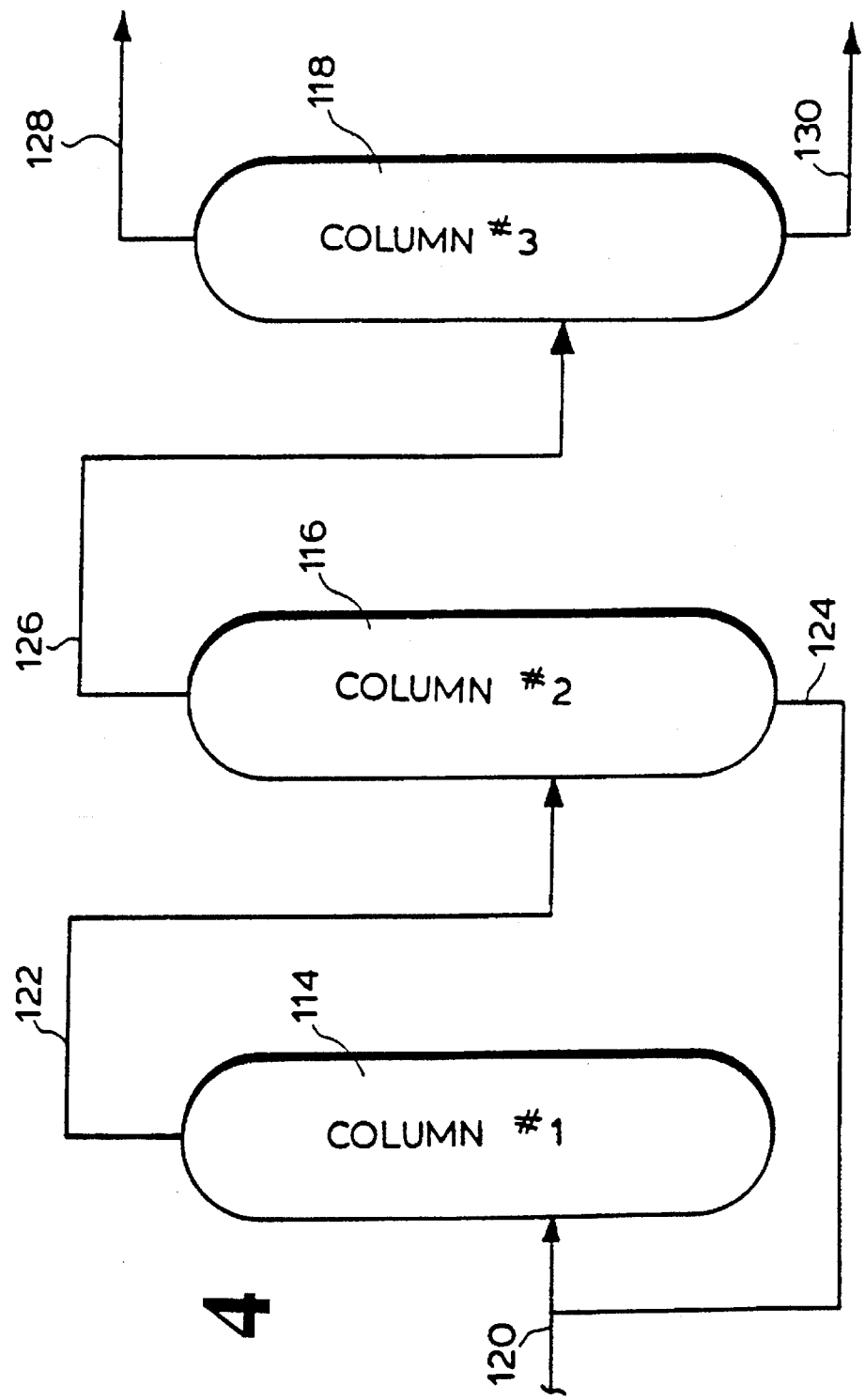
FIG. 4 is a schematic of the multi-stage fractional distillation system for separating components of the anesthetic absorbed by the canister coupled to the anesthetic machine.

Regardless of the composition of the liquid 108, it is important to purify it before reuse. In accordance with standard practice, anesthetics must have a high purity level normally in excess of 90% providing remaining impurities are non-toxic. To achieve that purity, the liquid 108 is subjected to fractional distillation. A preferred system is shown in FIG. 4 consisting of a multi-stage fractional distillation comprising three columns 114, 116 and 118. The liquid 108 is fed to column 114 via line 120. Sufficient heat is applied to the bottom of column 114 to cause the liquid 108 to boil and provide a vapor take-off in line 122. The vapor 122 is fed to column 116 where heat is applied to cause boiling of the vapor 122 as it condenses in column 116. The bottoms of columns 116 are removed via line 124 for recycle with new product into column 114. The vapors removed from column 116 via line 126 are fed to column 118. The vapors in line 126 condense in column 118 and with heat supplied thereto, cause boiling resulting in a take-off of two fractions, one in vapor phase in line 128 and secondly in liquid phase in line 130. Assuming that two anesthetics are in the liquid 108, the system of FIG. 4 separates them to provide desired purities in the lines 128 and 130. For example, with Forane and Ethrane, there is a difference in boiling points of approximately 8° C. which is sufficient to provide separation of the Ethrane from the Forane.

Bacteria is present in the patient exhalent. It has been found, however, that a bacteria in the patient exhalent is not adsorbed on the silicalite material to any appreciable extent. Hence, the anesthetic produced by fractional distillation and particularly as provided in lines 128 and 130 is not contaminated and is ready for reuse. In accordance with this invention, an inexpensive process and apparatus is provided for what in essence is the manufacture of anesthetic gases from mixtures which are normally discharged to the atmosphere. Significant economic advantages are realized.

Without limiting the scope of the appended claims, the following examples exemplify preferred aspects of the inventive process.

EXAMPLE 1

A canister of the type shown in FIG. 2 was subjected to a known flow rate of air with a known concentration of the anesthetic isoflurane while monitoring the inlet and outlet concentration of isoflurane in the canister outlet until saturation of the adsorbent in the canister was detected by breakthrough of the adsorption front. The apparatus was set up to generate a constant concentration of isoflurane in the air stream. The source of air was from a cylinder of "Zero" grade air a portion of the air metered through a flow meter was passed through two midget impingers each containing 15 ml of the anesthetic isoflurane. A third impinger prevented droplets of the isoflurane from being carried over and into the air stream. The isoflurane saturated air was then mixed with the zero air. The total flowrate was measured with a second flow meter. A dry gas meter was installed at the canister outlet to provide confirmation of the flow rate indicated by the upstream flow meter. The outlets and inlets were sampled periodically throughout the tests by way of a Miran (trade mark) 1A infrared analyzer. This instrument is a variable wavelength, variable pathlink analyzer capable of measuring isoflurane to concentrations well below 1 ppm. The instrument was calibrated before use to provide accurate readouts of the inlet and outlet concentrations of the canister.

Figure 5:
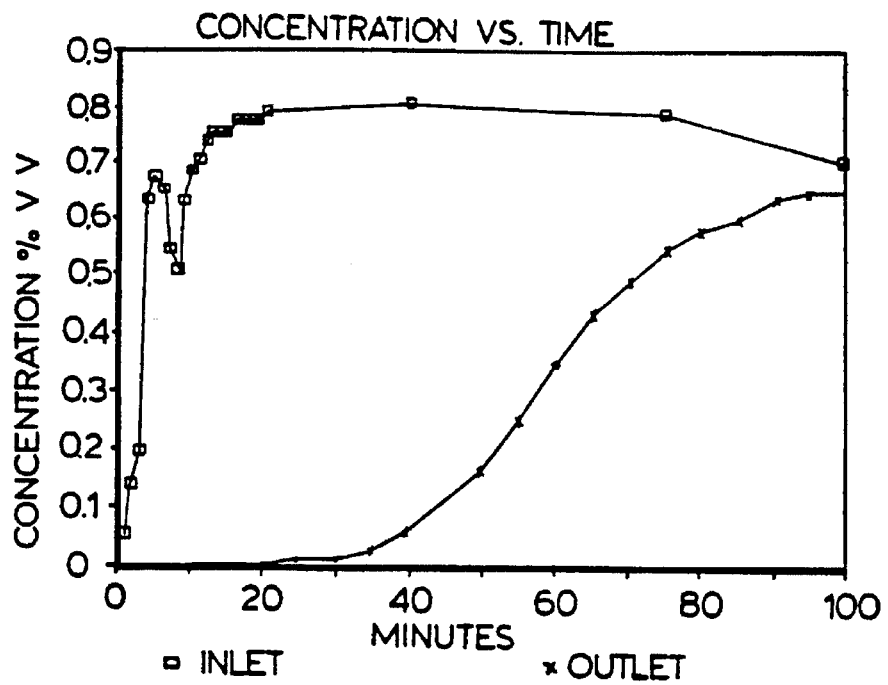
FIG. 5 is a plot of the inlet and outlet concentrations versus time for an airstream saturated with isoflurane passed into a canister of adsorbent material.

FIG. 5 is a plot of the inlet and outlet concentrations versus time at the canister. The inlet concentration was about 0.77% by volume for most of the program and the average flow rate was approximately 5.2 meters per minute. Breakthrough started to occur after about 30 minutes. The canister appeared to be fully saturated after about 100 minutes. At that point the outlet value for isoflurane concentration was only slightly less than the inlet value. The inlet value dropped because most of the isoflurane had been evaporated. There were 8 ml of isoflurane remaining in the impingers at the end program.

Figure 6:
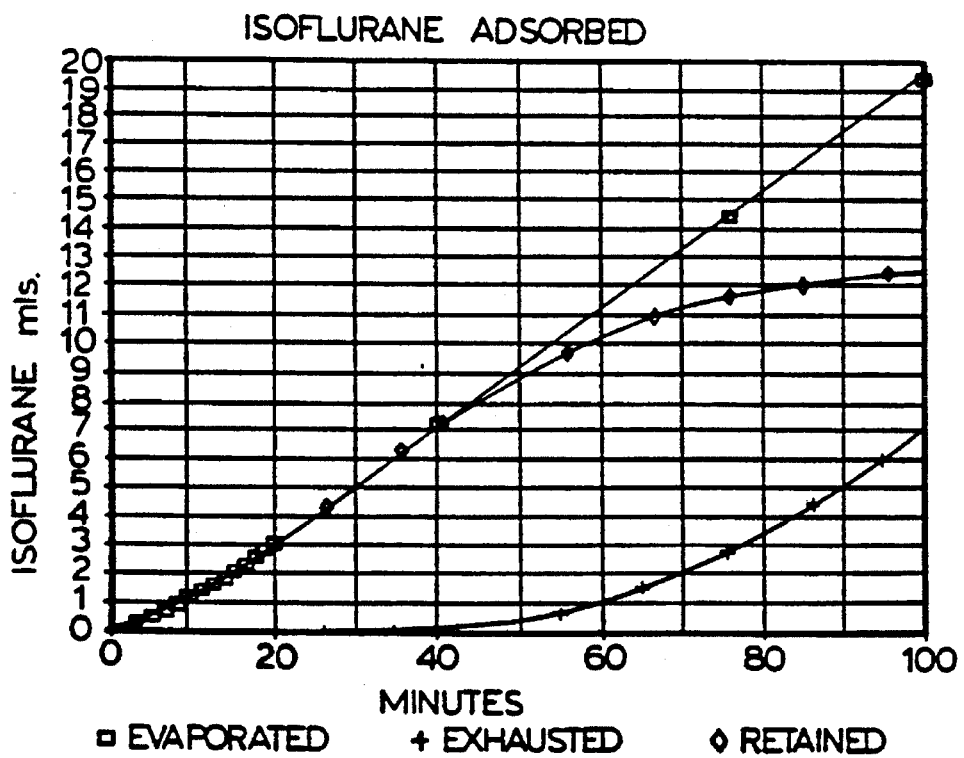
FIG. 6 is a plot of the net amounts of isoflurane evaporated, exhausted and retained in the canister versus time.

FIG. 6 is a plot of the net amounts of isoflurane evaporated, exhausted and retained versus time as calculated from the measured flow of isoflurane concentrations. The figure shows that about 19.5 ml were evaporated and about 12.7 ml were expected to have been adsorbed by the adsorbent in the canister at the end of the test run.

The canister of adsorbent was regenerated by use of an apparatus of the type shown in FIG. 3. The canister was heated in an oven to a temperature of approximately 140° C. The nitrogen gas passed through the canister was at a flow rate of approximately 1.3 liters per minute during regeneration. During such regeneration the nitrogen gas emerging from the coal trap was monitored for isoflurane.

Figure 7:
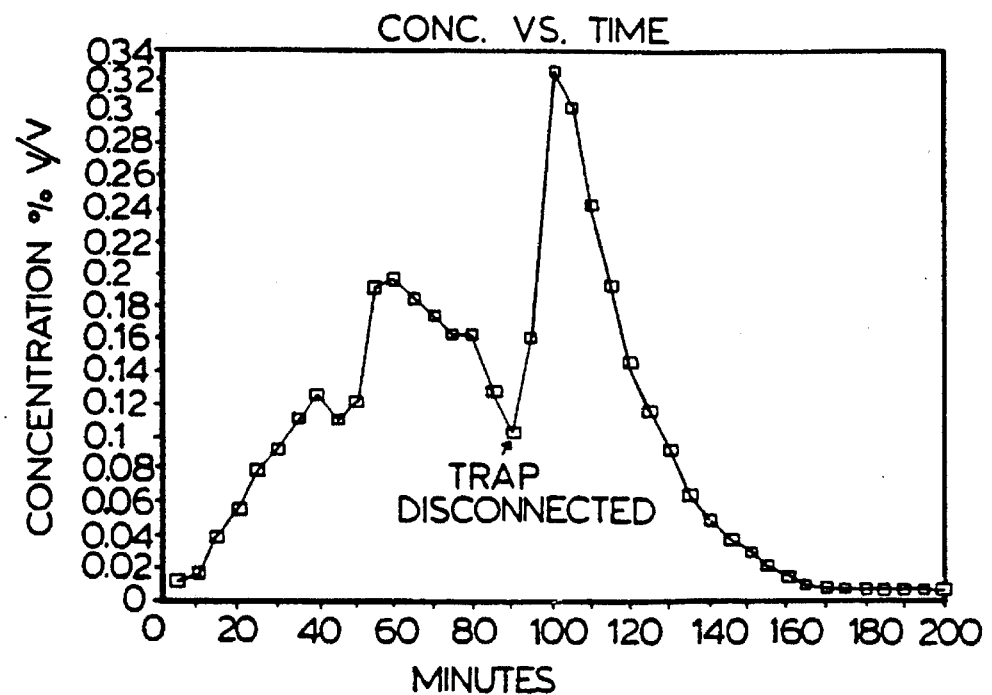
FIG. 7 is a plot of the concentration versus time of concentration of isoflurane in the purging gas stream exiting from the recovery system.

FIG. 7 is a plot of the concentration versus time for the monitored isoflurane concentration in the emerging nitrogen gas stream.

Figure 8:
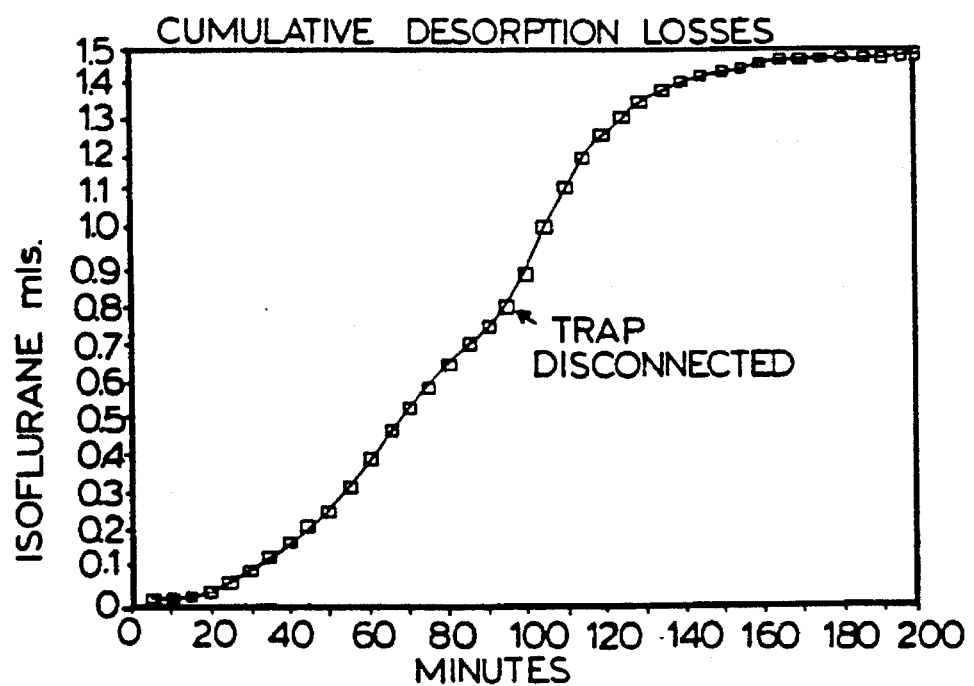
FIG. 8 is a plot versus time of the net volume of isoflurane lost in the regenerative gas stream exiting the recovery system.

FIG. 8 is a plot of the net volume of isoflurane lost versus time based on a flow rate of the 1.3 liters per minute of the regeneration gas.

The volume of isoflurane recovered from the flow trap was 11 ml. The amount expected was 12.7 ml.–1.5 ml.=11.2 mls. No water was recovered as expected since dry air was used. Furthermore, the adsorbent is principally hydrophobic. The results of the tests are therefore summarized in the following Table 1.

TABLE 1

| Laboratory Test Results - Summary | | |
| --- | --- | --- |
| Average inlet concentration | 0.76% | |
| Amount of Isoflurane in impinger | 30.0 | mls |
| Amount remaining | 8.0 | mls |
| Calculated isoflurane entering canister | 19.5 | mls |
| Isoflurane exhausted | 6.7 | mls |
| Amount of isoflurane expected | 12.7 | mls |
| Amount lost during desorption | 1.5 | mls |
| Net amount expected from recovery | 11.2 | mls |
| Actual amount recovered | 11.0 | mls |

Approximately 90% of the isoflurane was recovered by thermal desorption using a low purge flow rate for the purging gas. According to this particular set up the canister capacity for isoflurane is approximately 13 mls or 18 grams of the isoflurane. The volume of adsorptive material in the canister was approximately 185 grams of the SR-115 high silica zeolite adsorbent material.

EXAMPLE 2

The procedure of Example 1 was repeated with a view to establishing what the effect of the presence of water vapour in the gas stream had on the adsorption of the anesthetic gases. An impinger, containing water, was used to add moisture to the gas stream carrying the anesthetic gases. The average absolute humidity of 2.2% v/v was established. The inlet concentration of isoflurane was 0.84% by volume and the average flowrate was 5.2 liters per minute. Breakthrough occurred in approximately 25 minutes and the canister was completely saturated after approximately 78 minutes. Approximately 12.1 mls of isoflurane was adsorbed in the canister which is similar to the amount adsorbed in Example 1 under similar flowrate conditions. Hence the presence of moisture did not appreciably affect the adsorption of isoflurane.

The procedure of Example 1 was followed to desorb the isoflurane from the canister. Similar volume of isoflurane was recovered along with a minimal volume of water. Fractional distillation was used to separate the isoflurane from the water.

EXAMPLE 3

As the canister approaches saturation with adsorbed isoflurane continued passage of the gas stream through the canister has the potential for stripping isoflurane from the canister. The following procedure was established to determine if stripping could occur. A canister with 185 grams of silicalite was saturated with isoflurane. Air was then passed through the canister at a rate of about 6 liters per minute. The air at the exit of the canister was monitored for isoflurane using the Miran (trade mark) analyzer. At the beginning of the passage of the air stream, approximately 1.5 ml of isoflurane was removed from the saturated canister. Thereafter there was a nearly constant but extremely low concentration of isoflurane detected at the exit of the canister. This low concentration could not be accurately measured but was estimated to be at about 0.01 to 0.02% v/v for approximately 0.2 ml of liquid isoflurane per hour. Stripping of isoflurane from saturated or partially saturated canisters is therefore avoided and does not have a significant impact on the net amount of isoflurane that can be recovered from a gas stream.

EXAMPLE 4

Several canisters were used in a "real" situation by coupling the individual canisters to anesthetic machines which were in use at the Toronto General Hospital. Recovery of isoflurane from these canisters by thermal desorption in accordance with the procedure of Example 1 revealed that certain impurities were appearing in the recovered mixture. To determine the extent of impurities the following procedure was followed.

A new canister was loaded with 185 grams silicalite and regenerated at 120 degrees centigrade before use. The clean canister was coupled to a new anesthetic machine which was then put into use. After saturation of the canister it was then subjected to the procedure of Example 1 for recovery of the isoflurane. Recovery was carried out a desorption temperature of 120 degrees centigrade. The impurities identified in the recovered mixture were as follows:
1. 1-1-1-trifluoro-2-chloroethane;
2. bromochloro-1-1-difluoroethylene;
3. ethanal;
4. ethylene oxide;
5. trichlorofluoromethane;
6. dichlorodifluoromethane;
7. isopropyl alcohol;
8. 2-2-2 trifluoroethanol.

The fact that the above impurities appeared as desorbed from the adsorbent indicates that the high silica zeolite, adsorbent is capable of absorbing a variety of halogenated hydrocarbons and in turn desorbing such compounds at suitable desorption temperatures. It is thought that impurity #8 is the result of the degradation of the isoflurane. Impurity #2 is thought to be a breakdown product of halothane, ethanol (acetaldehyde) is possibly present as a patient exhalent, ethylene oxide and isopropyl alcohol are common chemicals used as disinfectants in the hospital. Impurities 5 and 6 are commonly known as Freon 11 (trade mark) and Freon 12 (trade mark). It is believed these compounds were present in the new anesthetic machine as potential filler gases, however, the presence of such gases indicate that these types of halogenated hydrocarbons are adsorbed onto the adsorbent of the canister and can be subsequently desorbed by temperature desorption.

Although the use of this canister has been demonstrated in association with an anesthetic machine, it is appreciated that the canister may be used in other systems to adsorb other types of halogenated hydrocarbons such as those commonly used as solvents, blowing agents, refrigerants, aerosol propellants and the like. Suitable systems may be set up to collect the vapours of these various agents and direct them through canisters which function in the same manner as the canisters specifically exemplified. Canisters can then be subjected to temperature desorption to provide for recovery and subsequent purification of the adsorbed halogenated hydrocarbons.

Although preferred embodiments of the invention have been described herein in detail, it will be understood by those skilled in the art that variations may be made thereto without departing from the spirit of the invention or the scope of the appended claims.

The Embodiments of the Invention in which an Exclusive Property or Privilege is Claimed are Defined as Follows:

1. Apparatus for the recovery of anesthetic gas comprising halogenated hydrocarbons comprising:

(A) a cannister for use in adsorbing halogenated hydrocarbons from a gas stream passed through said cannister, said cannister having a peripheral side wall, a first end wall with an inlet port and a second end wall with an outlet port, a first fine mesh screen spaced from said first end wall and closing off a first cannister end, a second fine mesh screen spaced from said second end wall and closing off a second cannister end, hydrophobic molecular sieve granular adsorbents being packed in said cannister between said first and second screens, said molecular sieve adsorbents having pore diameters large enough to permit molecules of the halogenated hydrocarbons to pass therethrough and be selectively adsorbed in the large internal cavities of the crystal framework, whereby the halogenated hydrocarbons are selectively removed from the gas stream, said first and second screens having a mesh sizing to retain said granular material in said cannister, means for resiliently urging one of said first or second screens towards the other to compress such granular material between said screens;

(B) an anesthetic machine having an exhaust port connected by conduit means to said inlet port of said cannister for passage of anesthetic gas from said anesthetic machine to said cannister, said conduit means comprising a shut off valve;

(C) an exhaust line communicating with the exhaust port of said cannister;

(D) an anesthetic sensor in said exhaust line to sense the presence of anesthetics in said exhaust line, said anesthetic sensor connected via a signal line to said anesthetic machine; and (E) bypass means for passing anesthetic gas from the anesthetic machine to the exhaust line without passing through the cannister, said bypass means comprising a control valve.

2. A canister of claim 1, wherein said adsorbent material has a pore size of approximately 6 angstroms.

3. A canister of claim 1 wherein said canister walls are formed of a corrosion resistant metal.

4. An apparatus for regenerating said canister of claim 1 comprising means for connecting an incoming line of nitrogen gas or air to said inlet port, means for heating said nitrogen gas or air in said incoming line to a temperature in the range of 30° C. to 150° C., means for connecting an outgoing line to said outlet port and means for measuring temperature in said outgoing line.

5. An apparatus of claim 4, wherein said outgoing line is connected to a condenser and means for collecting liquid from said condenser.

* * * * *